US008738610B2

(12) United States Patent
Anderson

(10) Patent No.: US 8,738,610 B2
(45) Date of Patent: May 27, 2014

(54) APPARATUS, SYSTEM AND METHOD FOR RAPID COHORT ANALYSIS

(75) Inventor: David R. Anderson, Chaska, MN (US)

(73) Assignee: Ingenix, Inc., Eden Prairie, MN (US)

( * ) Notice: Subject to any disclaimer, the term of this patent is extended or adjusted under 35 U.S.C. 154(b) by 686 days.

(21) Appl. No.: 12/605,697

(22) Filed: Oct. 26, 2009

(65) Prior Publication Data

US 2010/0114900 A1 May 6, 2010

Related U.S. Application Data

(60) Provisional application No. 61/108,428, filed on Oct. 24, 2008.

(51) Int. Cl.
*G06F 7/06* (2006.01)
*G06F 7/02* (2006.01)

(52) U.S. Cl.
USPC ............................ 707/722; 707/737; 707/758

(58) Field of Classification Search
None
See application file for complete search history.

(56) References Cited

U.S. PATENT DOCUMENTS

| | | | | |
|---|---|---|---|---|
| 7,516,111 | B2 | 4/2009 | Samson et al. | 706/1 |
| 7,672,950 | B2 | 3/2010 | Eckardt, III et al. | 707/10 |
| 7,895,210 | B2 * | 2/2011 | Bohn et al. | 707/741 |
| 2004/0122707 | A1 * | 6/2004 | Sabol et al. | 705/2 |
| 2005/0216312 | A1 * | 9/2005 | Bellin et al. | 705/3 |
| 2006/0271401 | A1 * | 11/2006 | Lassetter et al. | 705/2 |
| 2007/0282610 | A1 | 12/2007 | Luss et al. | 726/2 |
| 2010/0021888 | A1 * | 1/2010 | Ahuja et al. | 435/6 |
| 2011/0191343 | A1 * | 8/2011 | Heaton et al. | 707/737 |

OTHER PUBLICATIONS

International Search Report and Written Opinion, in Int. App. No. PCT/US2009/62085, mailed Dec. 10, 2009.

* cited by examiner

*Primary Examiner* — Ajay Bhatia
*Assistant Examiner* — Miranda Huang
(74) *Attorney, Agent, or Firm* — Fulbright & Jaworski LLP

(57) ABSTRACT

An apparatus, system, and method for rapid cohort analysis. In one embodiment, the apparatus includes an interface and a processor. The interface may receive an identifier of a first index attribute. The processor may search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records.

16 Claims, 11 Drawing Sheets

1000

| DECM_CODE | CODE_DESC | PRIMARY_COUNT | COHORT_COUNT | ALL_IN_PRIMARY_COUNT | ALL_IN_COHORT_COUNT | p_OR | q_OR |
|---|---|---|---|---|---|---|---|
| 746.02 | CONG PULMON VALVE STENOS | 233 | 1 | 38957 | 38957 | 0.00598 | 0.00003 |
| 745.2 | TETRALOGY OF FALLOT | 199 | 1 | 38957 | 38957 | 0.00511 | 0.00003 |
| 745.10 | COMPL TRANSPOS GREAT VES | 45 | 0 | 38957 | 38957 | 0.00116 | 0.00000 |
| 746.01 | CONG PULMON VALV ATRESIA | 38 | 0 | 38957 | 38957 | 0.00098 | 0.00000 |
| 996.83 | COMPL HEART TRANSPLANT | 34 | 0 | 38957 | 38957 | 0.00087 | 0.00000 |
| 745.11 | DOUBLE OUTLET RT VENTRIC | 30 | 0 | 38957 | 38957 | 0.00077 | 0.00000 |
| 746.83 | INFUNDIB PULMON STENOSIS | 25 | 0 | 38957 | 38957 | 0.00064 | 0.00000 |
| 282.62 | HB-S DISEASE WITH CRISIS | 23 | 0 | 38957 | 38957 | 0.00059 | 0.00000 |
| 745.0 | COMMON TRUNCUS | 21 | 0 | 38957 | 38957 | 0.00054 | 0.00000 |
| 746.81 | CONG SUBAORTIC STENOSIS | 21 | 0 | 38957 | 38957 | 0.00054 | 0.00000 |
| 745.3 | COMMON VENTRICLE | 18 | 0 | 38957 | 38957 | 0.00046 | 0.00000 |
| 427.42 | VENTRICULAR FLUTTER | 18 | 0 | 38957 | 38957 | 0.00046 | 0.00000 |
| 417.8 | PULMON CIRCULAT DIS NEC | 17 | 0 | 38957 | 38957 | 0.00044 | 0.00000 |
| 746.2 | EBSTEIN'S ANOMALY | 16 | 0 | 38957 | 38957 | 0.00041 | 0.00000 |
| 425.5 | ALCOHOLIC CARDIOMYOPATHY | 16 | 0 | 38957 | 38957 | 0.00041 | 0.00000 |
| 246.0 | DIS THYROCALCITON SECRET | 16 | 0 | 38957 | 38957 | 0.00041 | 0.00000 |
| 753.13 | POLYCYST KID-AUTOSOM DOM | 15 | 0 | 38957 | 38957 | 0.00039 | 0.00000 |
| 746.5 | CONGEN MITRAL STENOSIS | 14 | 0 | 38957 | 38957 | 0.00036 | 0.00000 |
| 745.12 | CORRECT TRANSPOS GRT VES | 14 | 0 | 38957 | 38957 | 0.00036 | 0.00000 |
| 42821 | ACUTE SYSTOLIC HEART FAI | 14 | 0 | 38957 | 38957 | 0.00036 | 0.00000 |

APPARATUS, SYSTEM AND METHOD FOR RAPID COHORT ANALYSIS

CROSS REFERENCE TO RELATED APPLICATIONS

This application claims the benefit of U.S. Provisional Application No. 61/108,428 filed Oct. 24, 2008, the entire contents of which is specifically incorporated herein by reference without disclaimer.

BACKGROUND OF THE INVENTION

1. Field of the Invention

This invention relates to health related data analysis and more particularly relates to an apparatus system and method for rapid cohort analysis.

2. Description of the Related Art

Most corporations, including health insurance corporations, maintain a high volume of data. Such data may be analyzed and exploited for valuable information regarding business trends, and other important statistics. Data mining is a common strategy for identifying and analyzing such data.

There are many various forms of data mining. Custom analytic operations may be developed to meet specific needs. Alternatively, commercially available statistical analysis tools, such as Statistical Analysis Software (SAS) may be used to identify statistical trends in data.

Health insurance companies typically maintain databases of health insurance claim information, demographic information, and other data about health insurance plan members. Such information may be used to gain valuable insights into disease causes, progressions, and potential cures. Unfortunately, typical methods for analyzing such data are often cumbersome, costly, and require unworkably high processing times and resources.

The referenced shortcomings are not intended to be exhaustive, but rather are among many that tend to impair the effectiveness of previously known techniques disease management; however, those mentioned here are sufficient to demonstrate that the methodologies appearing in the art have not been satisfactory and that a significant need exists for the techniques described and claimed in this disclosure.

SUMMARY OF THE INVENTION

From the foregoing discussion, it should be apparent that a need exists for an apparatus, system, and method for rapid cohort analysis.

An apparatus for rapid cohort analysis is presented. In one embodiment, the apparatus includes an interface and a processor. The interface may receive an identifier of a first index attribute. The processor may search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records.

A system is also presented for rapid cohort analysis. In one embodiment, the system includes a data storage device configured to store a database comprising one or more records, each record having one or more attributes. The system may also include a server in data communication with the data storage device. The server may receive an identifier of a first index attribute, search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records.

In one embodiment, the server may narrow the first group of records according to a limiting criterion. In a further embodiment, the server may assign a first distinguishing identifier to each record in a subset of the first group of records in response to a determination that the subset of records have a common value for the second index attribute. The server may also assign a second distinguishing identifier to a record in the second group of records that corresponds to the first distinguishing identifier assigned to a record in the subset of the first group of records.

In one embodiment, the server may count distinct records in the first group of records and the second group of records. The server may also aggregate records from the first group and from the second group according to a selected attribute. In still another embodiment, the server may compute a probability in response to a ratio of a number of records in the first group having the selected attribute and a number of records in the second group having the selected attribute.

A method is also presented for rapid cohort analysis. The method in the disclosed embodiments substantially includes the steps necessary to carry out the functions presented above with respect to the operation of the described apparatus and system. In one embodiment, the method includes receiving an identifier of a first index attribute, searching a database for a first group of records associated with the first index attribute, searching the database for a second group of records, each record in the second group of records sharing a common second index attribute with a record in the first group of records, but not associated with the first index attribute, and calculating a statistic in response to information associated with the first group of records and the second group of records.

In a further embodiment, the method may include narrowing the first group of records according to a limiting criterion. The method may also include assigning a first distinguishing identifier to each record in a subset of the first group of records in response to a determination that the subset of records have a common value for the second index attribute. Additionally, the method may include assigning a second distinguishing identifier to a record in the second group of records that corresponds to the first distinguishing identifier assigned to a record in the subset of the first group of records.

In a further embodiment, calculating the statistic further comprises counting distinct records in the first group of records and the second group of records. Calculating the statistic may also include aggregating records from the first group and from the second group according to a selected attribute. Additionally, calculating the statistic may include computing a probability in response to a ratio of a number of records in the first group having the selected attribute and a number of records in the second group having the selected attribute.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one nonlimiting embodiment "substantially" refers to ranges within 10%, preferably within 5%, more preferably within 1%, and most preferably within 0.5% of what is specified.

The terms “comprise” (and any form of comprise, such as “comprises” and “comprising”), “have” (and any form of have, such as “has” and “having”), “include” (and any form of include, such as “includes” and “including”) and “contain” (and any form of contain, such as “contains” and “containing”) are open-ended linking verbs. As a result, a method or device that “comprises,” “has,” “includes” or “contains” one or more steps or elements possesses those one or more steps or elements, but is not limited to possessing only those one or more elements. Likewise, a step of a method or an element of a device that “comprises,” “has,” “includes” or “contains” one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10 is a table illustrating one embodiment of a statistic calculated by rapid cohort analysis;

DETAILED DESCRIPTION

Figure 1:
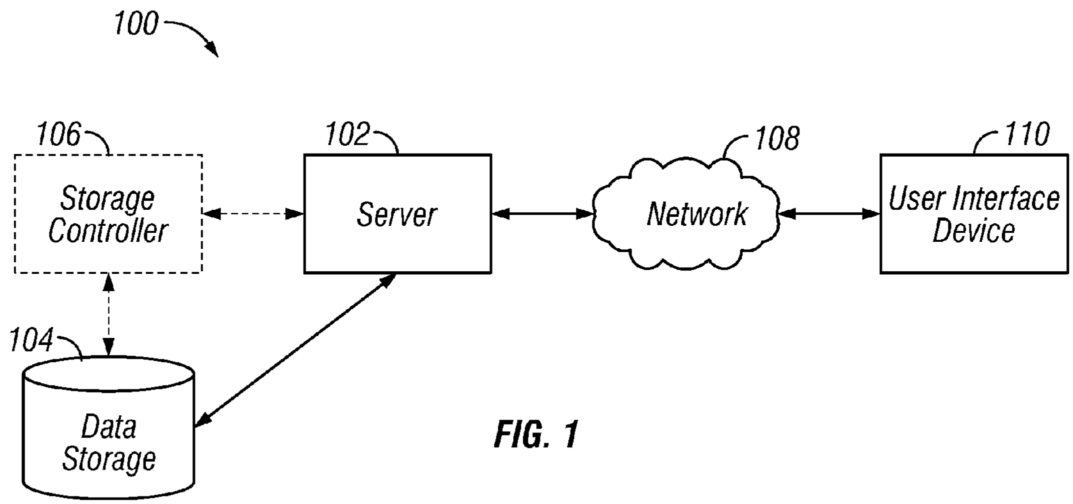
FIG. 1 is a schematic block diagram illustrating one embodiment of a system for rapid cohort analysis.

The invention and the various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

Reference throughout this specification to “one embodiment,” “an embodiment,” or similar language means that a particular feature, structure, or characteristic described in connection with the embodiment is included in at least one embodiment of the present invention. Thus, appearances of the phrases “in one embodiment,” “in an embodiment,” and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

FIG. 1 illustrates one embodiment of a system 100 for rapid cohort analysis. The system 100 may include a server 102 and a data storage device 104. In a further embodiment, the system 100 may include a network 108 and a user interface device 110. In still another embodiment, the system 100 may include a storage controller 106 or storage server configured to manage data communications between the data storage device 104 and the server 102 or other components in communication with the network 108. In an alternative embodiment, the storage controller 106 may be coupled to the network 108. In a general embodiment, the system 100 may store databases comprising records, perform searches of those records, and calculate statistics in response to information contained in those records. Specifically, the system 100 may aggregate records from a first group and from a second group according to a selected attribute. In still another embodiment, the server may compute a probability in response to a ratio of a number of records in the first group having the selected attribute and a number of records in the second group having the selected attribute.

In one embodiment, the user interface device 110 is referred to broadly and is intended to encompass a suitable processor-based device such as a desktop computer, a laptop computer, a Personal Digital Assistant (PDA), a mobile communication device or organizer device having access to the network 108. In a further embodiment, the user interface device 110 may access the Internet to access a web application or web service hosted by the server 102 and provide a user interface for enabling the service consumer (user) to enter or receive information. For example, the user may enter a first index attribute, a second index attribute, limiting criteria, a selected attribute for reporting a statistic, or the like.

The network 108 may facilitate communications of data between the server 102 and the user interface device 110. The network 108 may include any type of communications network including, but not limited to, a direct PC to PC connection, a local area network (LAN), a wide area network (WAN), a modem to modem connection, the Internet, a combination of the above, or any other communications network now known or later developed within the networking arts which permits two or more computers to communicate, one with another.

In one embodiment, the server 102 is may receive an identifier of a first index attribute, search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records. In a specific embodiment, the server 102 may include a high performance analytics server, such as an analytics server available from Netezza™ Corporation. Additionally, the server 102 may access data stored in the data storage device 104 via a Storage Area Network (SAN) connection, a LAN, a data bus, or the like.

The data storage device 104 may include a hard disk, including hard disks arranged in an Redundant Array of Independent Disks (RAID) array, a tape storage drive comprising a magnetic tape data storage device, an optical storage device, or the like. In one embodiment, the data storage device 104 may store health related data, such as insurance claims data, consumer data, or the like. The data may be arranged in a database and accessible through Structured Query Language (SQL) queries, or other data base query languages or operations.

Figure 2:
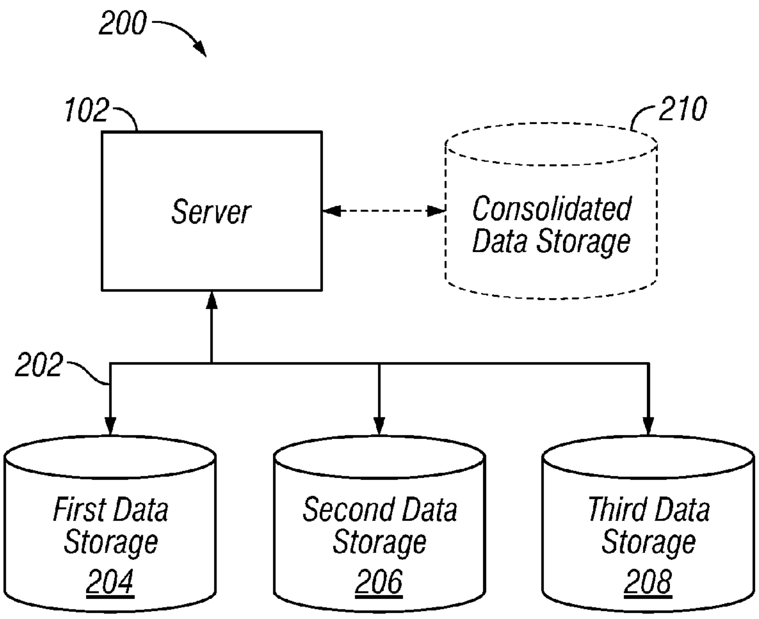
FIG. 2 is a schematic block diagram illustrating one embodiment of a database system for rapid cohort analysis.

FIG. 2 illustrates one embodiment of a data management system 200 configured to store and manage data for rapid cohort analysis. In one embodiment, the system 200 may include a server 102. The server 102 may be coupled to a data-bus 202. In one embodiment, the system 200 may also include a first data storage device 204, a second data storage device 206 and/or a third data storage device 208. In further embodiments, the system 200 may include additional data storage devices (not shown). In such an embodiment, each data storage device 204-208 may host a separate database of healthcare claims data, lab data, physical test data, disease progression data, demographic data, socioeconomic data, or the like. The customer information in each database may be keyed to a common field or identifier, such as an individual's name, social security number, customer number, or the like. Alternatively, the storage devices 204-208 may be arranged in a RAID configuration for storing redundant copies of the database or databases through either synchronous or asynchronous redundancy updates.

In one embodiment, the server 102 may submit a query to selected data storage devices 204-206 to collect a consolidated set of data elements associated with an individual or group of individuals. The server 102 may store the consolidated data set in a consolidated data storage device 210. In such an embodiment, the server 102 may refer back to the consolidated data storage device 210 to obtain a set of data elements associated with a specified individual. Alternatively, the server 102 may query each of the data storage devices 204-208 independently or in a distributed query to obtain the set of data elements associated with a specified individual. In another alternative embodiment, multiple databases may be stored on a single consolidated data storage device 210.

In various embodiments, the server 102 may communicate with the data storage devices 204-210 over the data-bus 202. The data-bus 202 may comprise a SAN, a LAN, or the like. The communication infrastructure may include Ethernet, Fibre-Chanel Arbitrated Loop (FC-AL), Small Computer System Interface (SCSI), and/or other similar data communication schemes associated with data storage and communication. For example, there server 102 may communicate indirectly with the data storage devices 204-210; the server first communicating with a storage server or storage controller 106.

In one example of the system 200, the first data storage device 204 may store data associated with insurance claims made by one or more individuals. The insurance claims data may include data associated with medical services, procedures, and prescriptions utilized by the individual. In one particular embodiment, the first data storage device 202 included insurance claims data for over 56 million customers of a health insurance company. The database included claims data spanning over 14 years. Of those 56 million members, 26 million had a five year history or more.

In one embodiment, the second data storage device 206 may store summary data associated with the individual. The summary data may include one or more diagnoses of conditions from which the individual suffers and/or actuarial data associated with an estimated cost in medical services that the individual is likely to incur. The third data storage device 208 may store customer service and program service usage data associated with the individual. For example, the third data storage device 208 may include data associated with the individual's interaction or transactions on a website, calls to a customer service line, or utilization of a preventative medicine health program. A fourth data storage device (not shown) may store marketing data. For example, the marketing data may include information relating to the individual's income, race or ethnicity, credit ratings, etc. In one embodiment, the marketing database may include marketing information available from a commercial direct marketing data provider.

The server 102 may host a software application configured for rapid cohort analysis. The software application may further include modules or functions for interfacing with the data storage devices 204-210, interfacing a network 108, interfacing with a user, and the like. In a further embodiment, the server 102 may host an engine, application plug-in, or application programming interface (API). In another embodiment, the server 102 may host a web service or web accessible software application.

Figure 3:
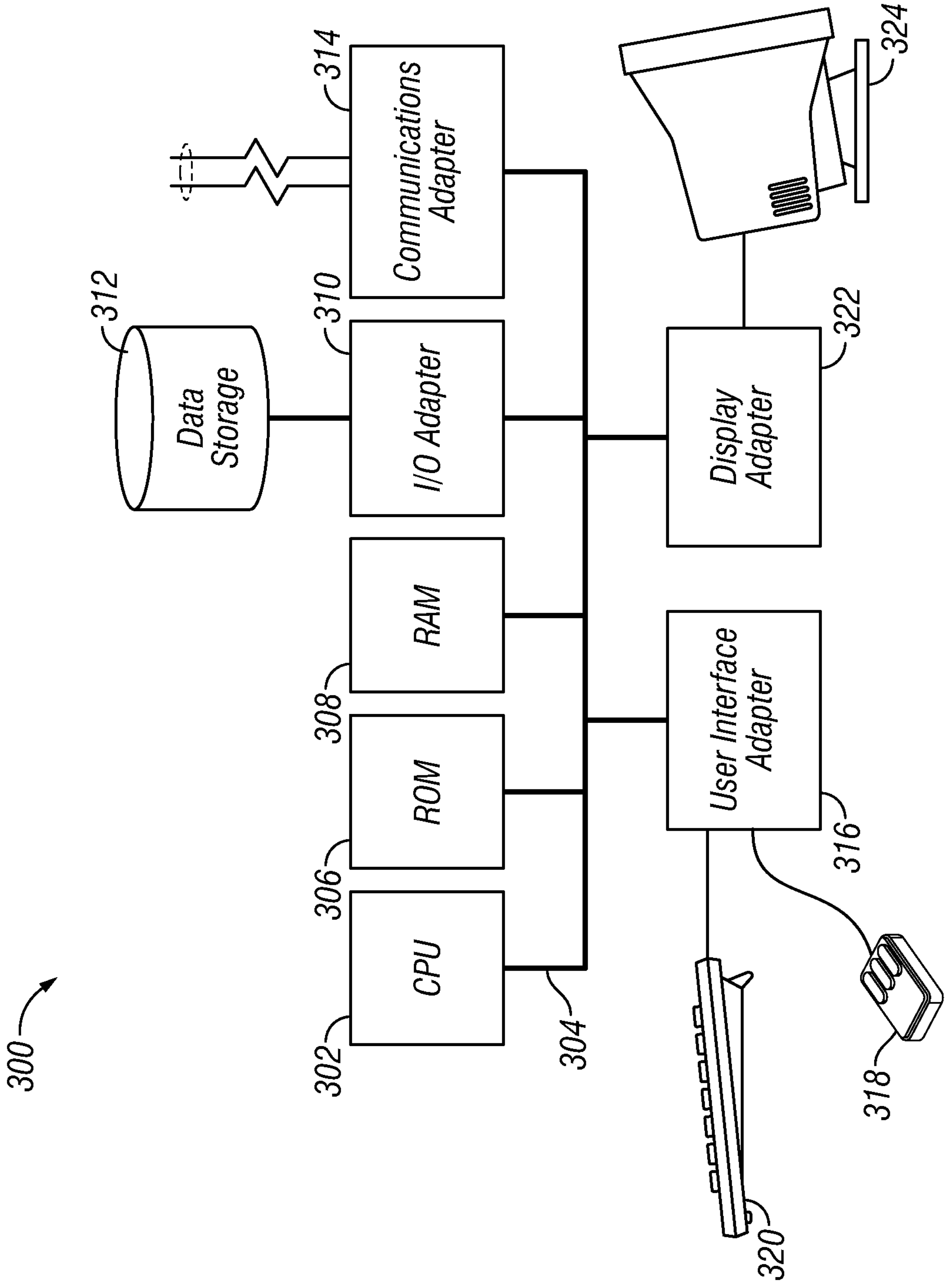
FIG. 3 is a schematic block diagram illustrating one embodiment of a computer system that may be used in accordance with certain embodiments of the system for rapid cohort analysis.

FIG. 3 illustrates a computer system 300 adapted according to certain embodiments of the server 102 and/or the user interface device 110. The central processing unit (CPU) 302 is coupled to the system bus 304. The CPU 302 may be a general purpose CPU or microprocessor. The present embodiments are not restricted by the architecture of the CPU 302, so long as the CPU 302 supports the modules and operations as described herein. The CPU 302 may execute the various logical instructions according to the present embodiments. For example, the CPU 302 may execute machine-level instructions according to the exemplary operations described below with reference to FIG. 8.

The computer system 300 also may include Random Access Memory (RAM) 308, which may be SRAM, DRAM, SDRAM, or the like. The computer system 300 may utilize RAM 308 to store the various data structures used by a software application configured for rapid cohort analysis. The computer system 300 may also include Read Only Memory (ROM) 306 which may be PROM, EPROM, EEPROM, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or user the interface adapter 316 may, in certain embodiments, enable a user to interact with the computer system 300 in order to input information for authenticating a user, identifying an individual, or receiving health profile information. In a further embodiment, the display adapter 322 may display a graphical user interface associated with a software or web-based application for rapid cohort analysis.

The I/O adapter 310 may connect to one or more storage devices 312, such as one or more of a hard drive, a Compact Disk (CD) drive, a floppy disk drive, a tape drive, to the computer system 300. The communications adapter 314 may be adapted to couple the computer system 300 to the network 106, which may be one or more of a LAN and/or WAN, and/or the Internet. The user interface adapter 316 couples user input devices, such as a keyboard 320 and a pointing device 318, to the computer system 300. The display adapter 322 may be driven by the CPU 302 to control the display on the display device 324.

The present embodiments are not limited to the architecture of system 300. Rather the computer system 300 is provided as an example of one type of computing device that may be adapted to perform the functions of server 102 and/or the user interface device 110. For example, any suitable processor-based device may be utilized including without limitation, including personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the described embodiments.

Figure 4:
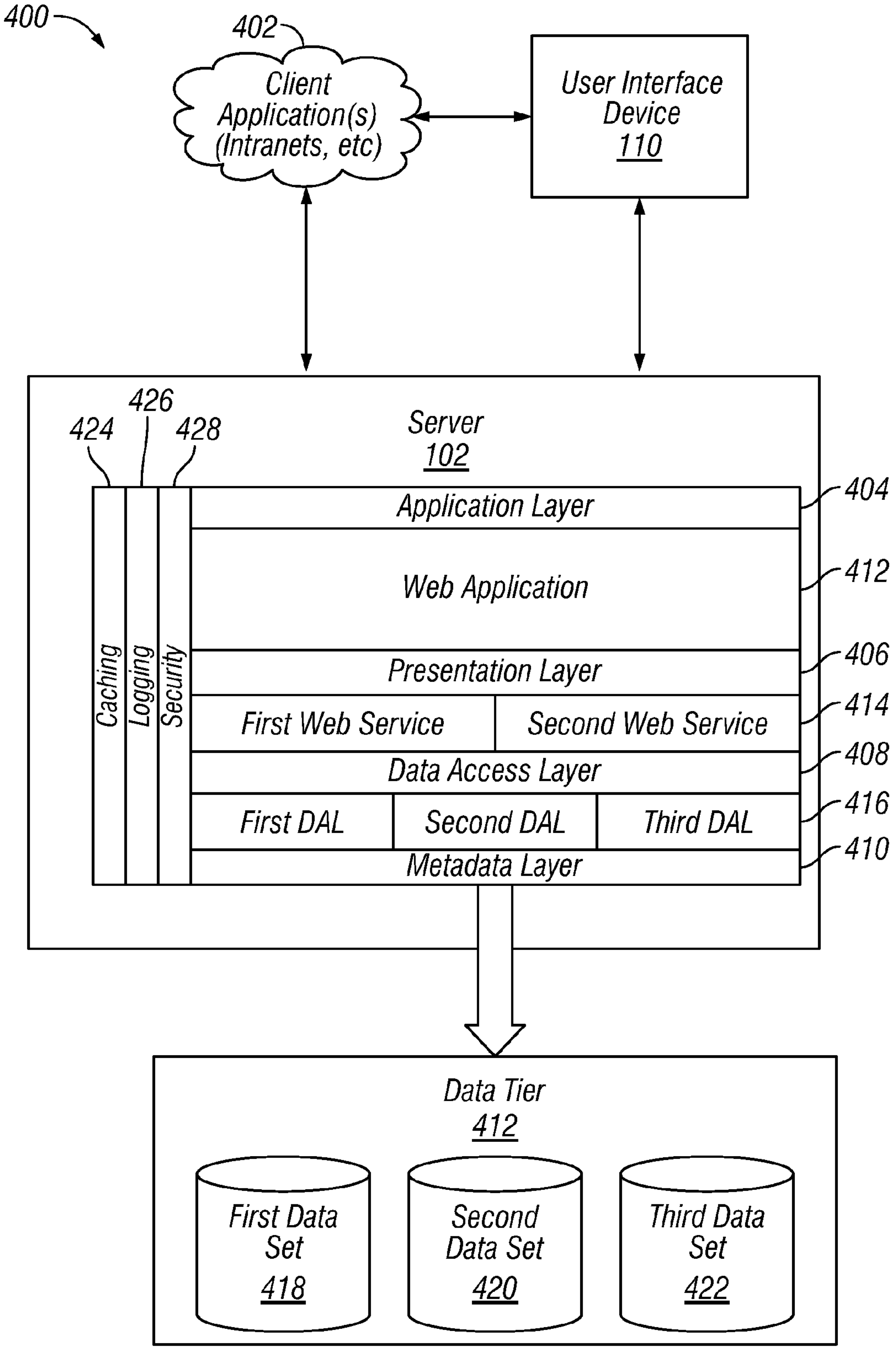
FIG. 4 is a schematic logical diagram illustrating the various layers of operation in a system for rapid cohort analysis.

FIG. 4 illustrates one embodiment of a network-based system 400 for rapid cohort analysis. In one embodiment, the network-based system 400 includes a server 102. Additionally, the network-based system 400 may include a user interface device 110. In still a further embodiment, the network-based system 400 may include one or more network-based client applications 402 configured to be operated over a network 108 including an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more data sets 422-422 that comprises a data layer or data tier 412. For example, a first data set 422, a second data set 420 and a third data set 422 may comprise data tier 412 that is stored on one or more data storage devices 204-208.

One or more web applications 412 may operate in the application layer 404. For example, a user may interact with the web application 412 though one or more I/O interfaces 318, 320 configured to interface with the web application 412 through an I/O adapter 310 that operates on the application layer. In one particular embodiment, a web application 412 may be provided for rapid cohort analysis that includes software modules configured to perform the steps of receiving an identifier of a first index attribute, searching a database for a first group of records associated with the first index attribute, searching the database for a second group of records, each record in the second group of records sharing a common second index attribute with a record in the first group of records, but not associated with the first index attribute, and calculating a statistic in response to information associated with the first group of records and the second group of records.

In a further embodiment, the server 102 may include components, devices, hardware modules, or software modules configured to operate in the presentation layer 406 to support one or more web services 414. For example, a web application 412 may access a web service 414 to perform one or more web-based functions for the web application 412. In one embodiment, a web application 412 may operate on a first server 102 and access one or more web services 414 hosted on a second server (not shown) during operation.

For example, a web application 412 for identifying cohorts and/or analyzing cohort data, or other information may access a first web service 414 for identifying a first group of individuals associated with a first index attribute, and a second web service 414 for identifying a second group of individuals that share one or more second index attributes, but are not associated with the first index attribute. The web services 414 may receive an indicant of the first index attribute. In response, the web service 414 may return a list of records associated with the index attribute, statistics, graphs, or the like. One of ordinary skill in the art will recognize various web-based architectures employing web services 414 for modular operation of a web application 412.

In one embodiment, a web application 412 or a web service 414 may access one or more of the data sets 418-422 through the data access layer 408. In certain embodiments, the data access layer 408 may be divided into one or more independent data access layers 416 for accessing individual data sets 418-422 in the data tier 412. These individual data access layers 416 may be referred to as data sockets or adapters. The data access layers 416 may utilize metadata from the metadata layer 410 to provide the web application 412 or the web service 414 with specific access to the data set 412.

For example, the data access layer 416 may include operations for performing a query of the data sets 418-422 to retrieve specific information for the web application 412 or the web service 414. In a more specific example, the data access layer 416 may include a query for records associated with individuals who have been diagnosed with diabetes or that are associated with an ICD-9 code associated with a diagnosis of diabetes.

Figure 5:
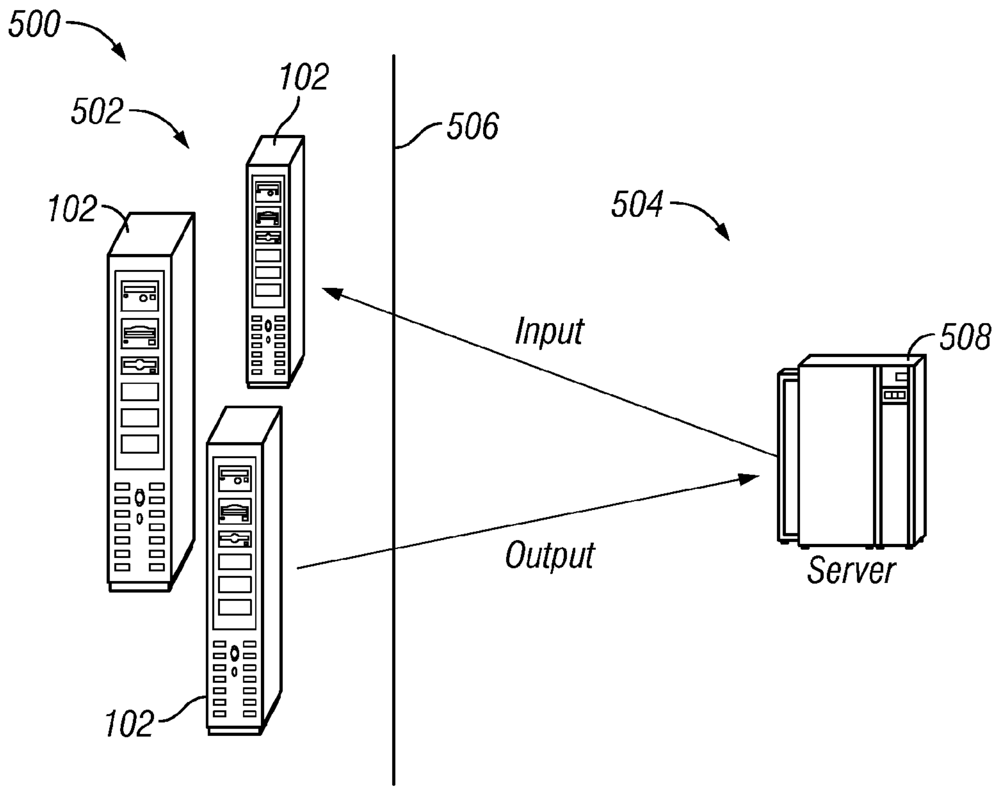
FIG. 5 is a schematic block diagram illustrating one embodiment of a distributed system for rapid cohort analysis.

FIG. 5 illustrates a further embodiment of a system 500 for rapid cohort analysis. In one embodiment, the system 500 may include a service provider site 502 and a client site 504. The service provider site 502 and the client site 504 may be separated by a geographic separation 506.

In one embodiment, the system 500 may include one or more servers 102 configured to host a software application 412 for rapid cohort analysis, or one or more web services 414 for performing certain functions associated with rapid cohort analysis. The system may further comprise a user interface server 508 configured to host an application or web page configured to allow a user to interact with the web application 412 or web services 414 for rapid cohort analysis. In such an embodiment, a service provider may provide hardware 102 and services 414 or applications 412 for use by a client without directly interacting with the client's customers.

Figure 6:
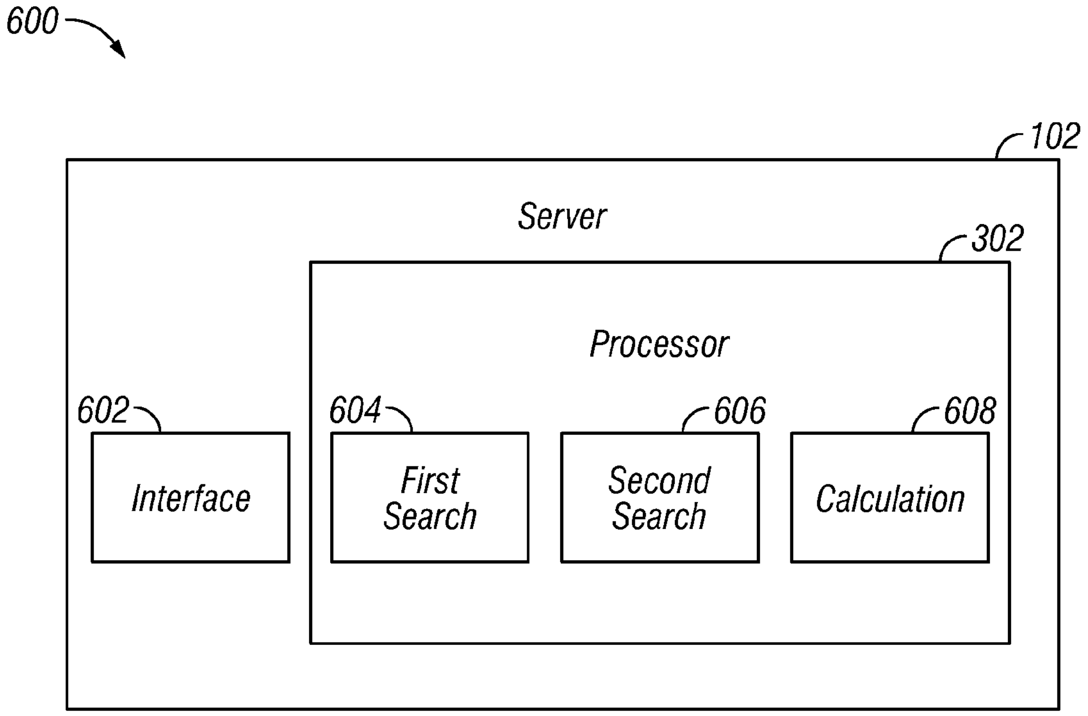
FIG. 6 is a schematic block diagram illustrating one embodiment of an apparatus for rapid cohort analysis.

FIG. 6 illustrates one embodiment of an apparatus 600 for rapid cohort analysis. In one embodiment, the apparatus 600 is a server 102 configured to load and operate software modules 602-608 configured for rapid cohort analysis. Alternatively, the apparatus 600 may include hardware modules 602-608 configured with analogue or digital logic, firmware executing FPGAs, or the like configured to receive an identifier of a first index attribute, search a database for a first group of records associated with the first index attribute, search the database for a second group of records, each record in the second group of records sharing a common second index attribute with a record in the first group of records, but not associated with the first index attribute, and calculating a statistic in response to information associated with the first group of records and the second group of records. In such embodiments, the apparatus 600 may include a processor 302 and an interface 602, such as an I/O adapter 310, a communications adapter 310, a user interface adapter 316, or the like.

In one embodiment, the processor 302 may include one or more software defined modules configured to search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records. In one embodiment, these modules may include a first search module 604, a second search module 606, and a calculation module 608.

The first index attribute and the second index attribute may, in certain circumstances, include a plurality of index attributes. This may be referred to as an "index signature." For example, it may be helpful for a user of the present apparatus, system, and method, to identify occurrences of a particular combination of diagnoses, events, characteristics, or the like. In such an example, a physician may desire to know the number of males over the age of 40 who have both diabetes and renal failure. Thus, the first index attribute in this example may include the diagnosis code for diabetes, as well as a diagnosis code for renal failure, an age attribute having a value over '40,' and a gender attribute having a value of 'male.' Similarly, the second index attribute may include a combination of a plurality of attributes, field values, characteristics, or variables. In certain aspects, the first group of records and the second group of records may differ in one index attribute (the first index attribute), such as a diagnosis of disease, but can share a combination of attributes (the second index attributes), such as age, gender, area, minority status, income level, etc.

In a further example, the first and second attributes may include a temporal component. For example, the first index attribute may include a temporal difference between two attributes. In such an embodiment, the trigger for the first index attribute would include the combination of two attributes separated by a specified time frame. In such an example, the first group of records may include all diabetics with a retinopathy within 1 year of diabetic onset (which could be either an ICD9 code or a lab reading or both) with another set of attribute of interest aggregated 1 to 5 years after the first retinopathy diagnosis. The second group of records (the cohort group) may include the entire patient population or could be limited to diabetics of the desired enrollment span who have not had a retinopathy.

Although the various functions of the server 102 and the processor 302 are described in the context of modules, the methods, processes, and software described herein are not limited to a modular structure. Rather, some or all of the functions described in relation to the modules of FIGS. 6-7 may be implemented in various formats including, but not limited to, a single set of integrated instructions, commands, code, queries, etc. In one embodiment, the functions may be implemented in database query instructions, including SQL, PLSQL, or the like. Alternatively, the functions may be implemented in software coded in C, C++, C#, php, Java, or the like. In still another embodiment, the functions may be implemented in web based instructions, including HTML, XML, etc.

Generally, the interface module 602 may receive user inputs and display user outputs. For example, the interface module 602 may receive an identifier of a first index attribute. The interface module may further receive identifiers of one or more second index attributes, limiting criterion, and other user inputs. In a further embodiment, the interface module 604 may display cohort analysis results. Such cohort analysis results may include statistics, tables, charts, graphs, recommendations, and the like.

Structurally, the interface module 602 may include one or more of an I/O adapter 310, a communications adapter 314, a user interface adapter 316, and/or a display adapter 322. The interface module 602 may further include I/O ports, pins, pads, wires, busses, and the like for facilitating communications between the processor 302 and the various adapters and interface components 310-324. The interface module may also include software defined components for interfacing with other software modules on the processor 302.

In one embodiment, the processor 302 may load and execute software modules configured to search the database for a first group of records associated with the first index attribute, search the database for a second group of records, each record in the second group of records sharing a common second index attribute with a record in the first group of records, but not associated with the first index attribute, and calculate a statistic in response to information associated with the first group of records and the second group of records. These software modules may include a first search module 604, a second search module 606, and a calculation module 608.

In a specific embodiment, the processor 302 may load and execute computer software configured to generate, retrieve, send, or otherwise operate SQL instructions. For example, the first search module 604 may communicate a first SQL query to the data storage device 104 which is configured to search the database for a first group of records associated with the first index attribute. The first index attribute may include a field value, such as a healthcare billing or diagnosis code stored in a database of healthcare insurance information. In a specific embodiment, the first search operation may identify a first group of individuals having records that include a specified ICD-9 diagnosis code. For example, the first search may identify a first group of records in the database associated with individuals that have been diagnosed with diabetes.

The second search module 606 may generate and/or communicate a second SQL query to the database in response to the results of the first SQL query. The second query may be configured to search the database for a second group of records, each record in the second group of records sharing a common second index attribute with a record in the first group of records, but not associated with the first index attribute. The second group of records may be cohorts of the first group of records. The second index attribute may include a separate field of data values stored in the records. For example, the second index attribute may include a field value that indicates certain specified characteristics of the individuals associated with the records, such as age, gender, minority status, a geographic feature, lab tests, lab results, other diseases or diagnoses, use of medication, a genetic feature (presence or absence of a genetic marker such as single nucleotide polymorphism, a specific genotype, a specific gene or gene cluster, a characteristic of a specific chromosome), and the like, or a combination thereof.

By way of example, the first search module 604 may identify a first group of individuals that have been diagnosed with diabetes or some other illness based on an ICD-9 field value associated with such a medical diagnosis. The second search module 606 may then identify cohorts for each individual or record identified by the first search. The cohorts may share one or more common second index attributes with the individuals or records identified in the first group, such as age, gender, or the like; however, the cohorts would not include the first index attribute. In this example, the cohorts may be the same age and gender as the individuals in the first group, but not have been diagnosed with diabetes.

In certain embodiments, for each record identified in the first group, the second search module 606 may identify one or more cohorts, for example, at least or about 2, 5, 10, 50, 100, 200 cohorts (or any range derivable therein) with a difference in the first index attribute but a matching second index attribute. For example, for each record associated with a diabetic subject, 100 non-diabetic cohorts may be identified for a match of age and gender. This aspect may reduce the noise in cohort matching and measurement of attributes to compare between matching records in the second group (primary) and the first group (cohort) by over-sampling.

In further embodiments, the cohort group can be sampled in a deterministic or random way by altering the analytic function of the second search module 606. For example, as shown in the SQL instructions described later, the cohort group may be sampled randomly based on internal data access with specific instructions like:

```
row_number( ) over (partition by age_at_onset2,year_of_onset2,
gender order by year_of_onset2) rn_inplay2
```

In another embodiment, the second search module 606 may identify the cohort group of records by forcing randomness into the cohort group, as exemplified by the instructions like:

```
row_number( ) over (partition by age_at_onset2,year_of_onset2,
gender order by random( ) ) rn_inplay2
```

In a further aspects, the sampling of the cohort group may be performed in a deterministic manner with predetermined individuals as matching cohorts, with exemplary instructions like:

```
row_number( ) over (partition by age_at_onset2,year_of_onset2,
gender order by individual_id) rn_inplay2
```

In a further embodiment, the first search module 604 and the second search module 606 may be integrated into a single search module. Specifically, a single set of SQL instructions may be used to both identify the first group of records and identify the cohorts. The benefits of this embodiment may include reduced system overhead, reduced search and analysis time, reduced labor for configuration and generation of queries, etc. For example, with a single integrated SQL query, a user may be able to obtain results for analysis in far less time than he/she might otherwise expect. Such an embodiment, would not require separate analysis and generation of separate queries for the first group and the second group. Consequently, a significant time savings may be realized.

In one embodiment, the calculation module 608 may calculate a statistic in response to information associated with the first group of records and the second group of records. For example, the calculation module may include analogue or digital logic, firmware, or software configured to carry out one or more calculations according to one or more predefined logic functions. In a further embodiment, the processor 302 may include a software defined calculation module 608 configured to perform analysis and calculation of statistics in response to the information and data retrieved from the database for the first group of records and the associated second group of cohort records.

In a specific embodiment, the first search module 604 and the second search module 606 may feed retrieved data into a spreadsheet configured to perform one or more calculations on the data. For example an Excel® spreadsheet may include one or more embedded functions or operations configured to calculate statistics such as averages, odds ratios and other probabilities, counts, summations, and the like. The data may be automatically imported into a spreadsheet using a macro, a software-based script, or the like. In an alternative embodiment, the calculation module 608 may include hard-coded or dynamically variable software functions for calculating such statistics and generating results for a user.

Figure 7:
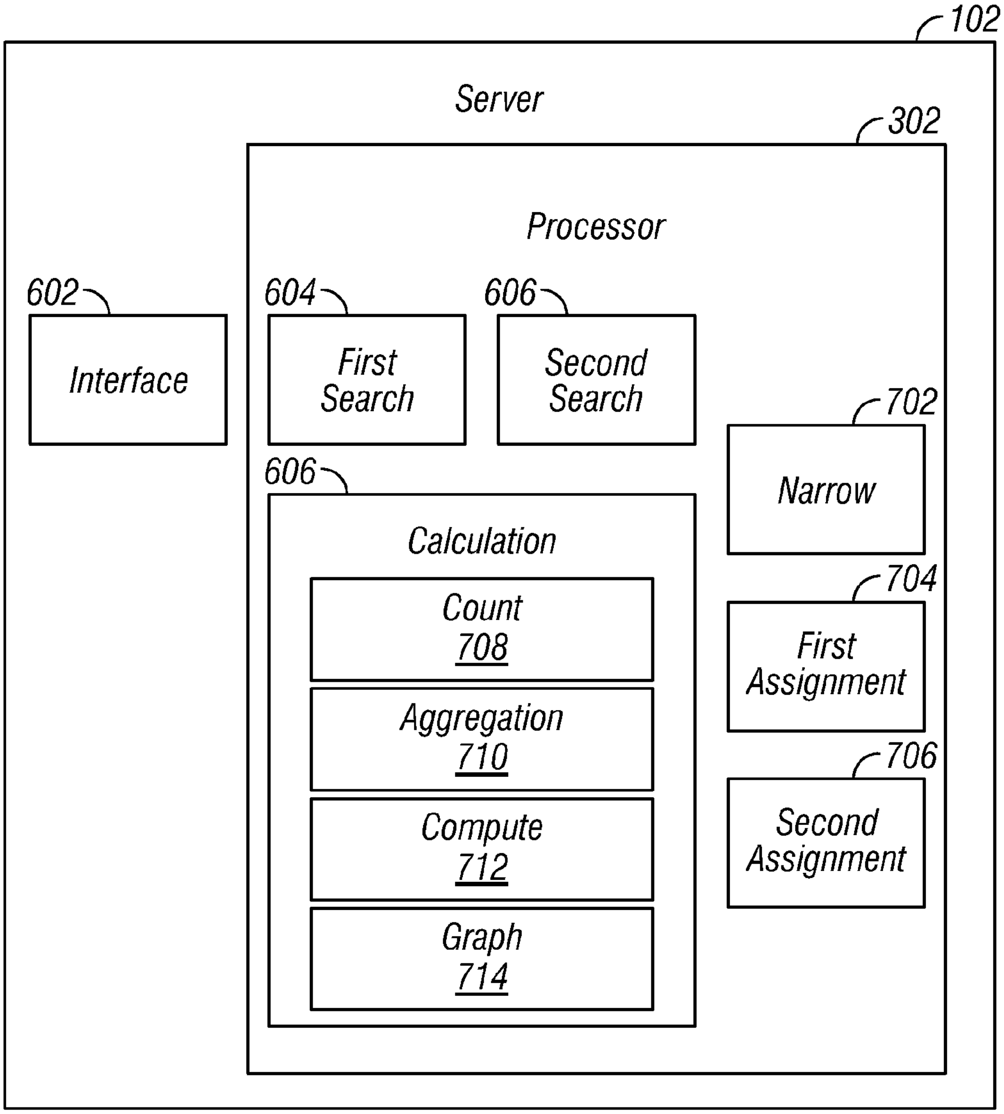
FIG. 7 is a schematic block diagram illustrating another embodiment of an apparatus for rapid cohort analysis.

FIG. 7 illustrates a further embodiment of an apparatus 600 rapid cohort analysis. The apparatus 600 may include a server 102 as described in FIG. 6. In a further embodiment, the processor 302 may include additional software defined modules. For example, the processor 302 may include a narrow module 702, a first assignment module 704, and a second assignment module 706. The calculation module 606 may further include a count module 708, an aggregation module 710, a compute module 712, and a graph module 714.

In a further embodiment, the narrow module 702 may narrow the first group of records according to a limiting criterion. The narrow module 702 may narrow the first group of records by restricting search parameters before the first search is performed. Alternatively, the narrow module 702 may filter, remove, or otherwise delete the search results according to the limiting criterion. In a certain embodiment, multiple limiting criteria may be used to restrict the scope of the returned search results. In one embodiment, a limiting criteria may include a field value, such as record date, age, gender, or the like.

In one embodiment, the server 102 may assign a first distinguishing identifier to each record in a subset of the first group of records in response to a determination that the subset of records have a common value for the second index attribute. For example, the processor 302 may include a first assignment module 704 configured to assign the first distinguishing identifier to the records. In an alternative embodiment, an SQL command generated by the server 102 or stored in RAM 308 or on the data storage device 312 may include instructions, that when executed by a storage controller 106 or the processor 302 on the server 102, may cause the first distinguishing identifier to be assigned to each of the matching records. In such an example, the SQL code may include instructions to search the database for records associated with a diagnosis code indicating diabetes or some other illness. If multiple search results have matching second index attributes, such as age, gender, or the like, the SQL instructions may include an operation to assign an incremental distinguishing identifier, such as a '1', '2', or '3' to each of the records in the subset of records having common second index attributes.

Similarly, the server 102 may assign a second distinguishing identifier to a record in the second group of records that corresponds to the first distinguishing identifier assigned to a record in the subset of the first group of records. This operation may be performed in similar ways as those described above with relation to the first distinguishing identifier. Specifically, a second assignment module 706 may make the assignment. Alternatively, an SQL operation embedded with the search may perform the assignment.

In one embodiment, the server 102 may include a count module 708 configured to count distinct records in the first group of records and the second group of records. The counting function may be implemented using a hardware-based counter. Alternatively, the counting function may be implemented in software. In a specific embodiment, the processor 302 may execute SQL instructions configured to provide the record count in response to search or query results. In such an embodiment, the counting function may be integrated with the search and assignment instructions into a single set of SQL commands or instructions.

In one embodiment, the server 102 may include an aggregation module 710 configured to aggregate records from the first group and from the second group according to a selected attribute. For example, the selected attribute shared between the first and the second group may be a temporal index date, such as a start date of certain event or occurrence, e.g., diagnosis, treatment, drug administration, procedures, lab tests, or the like. In certain embodiments, the temporal index date may be set by an event for each record (primary) in the first group (e.g., onset date of diabetes or insertion of a pacemaker) and set in an arbitrary manner for each matching record (cohort) in the second group (e.g. the same event date for each primary-cohort pair when the cohort in the second group is the same age as the primary). In other embodiments, the temporal index date may be set by an event for each record in the first group (e.g. onset date of diabetes, administration of a drug, perform a treatment or procedure, or insertion of a pacemaker) and may be set in a determined manner in the second group (e.g. the time the cohort shared a similar but different event, such as administration of a different drug, onset of a related but different treatment or procedure, or insertion of a different pacemaker brand). The index date could be seconds, hours, years, or a combination thereof, etc, depending on the event.

Figure 13:
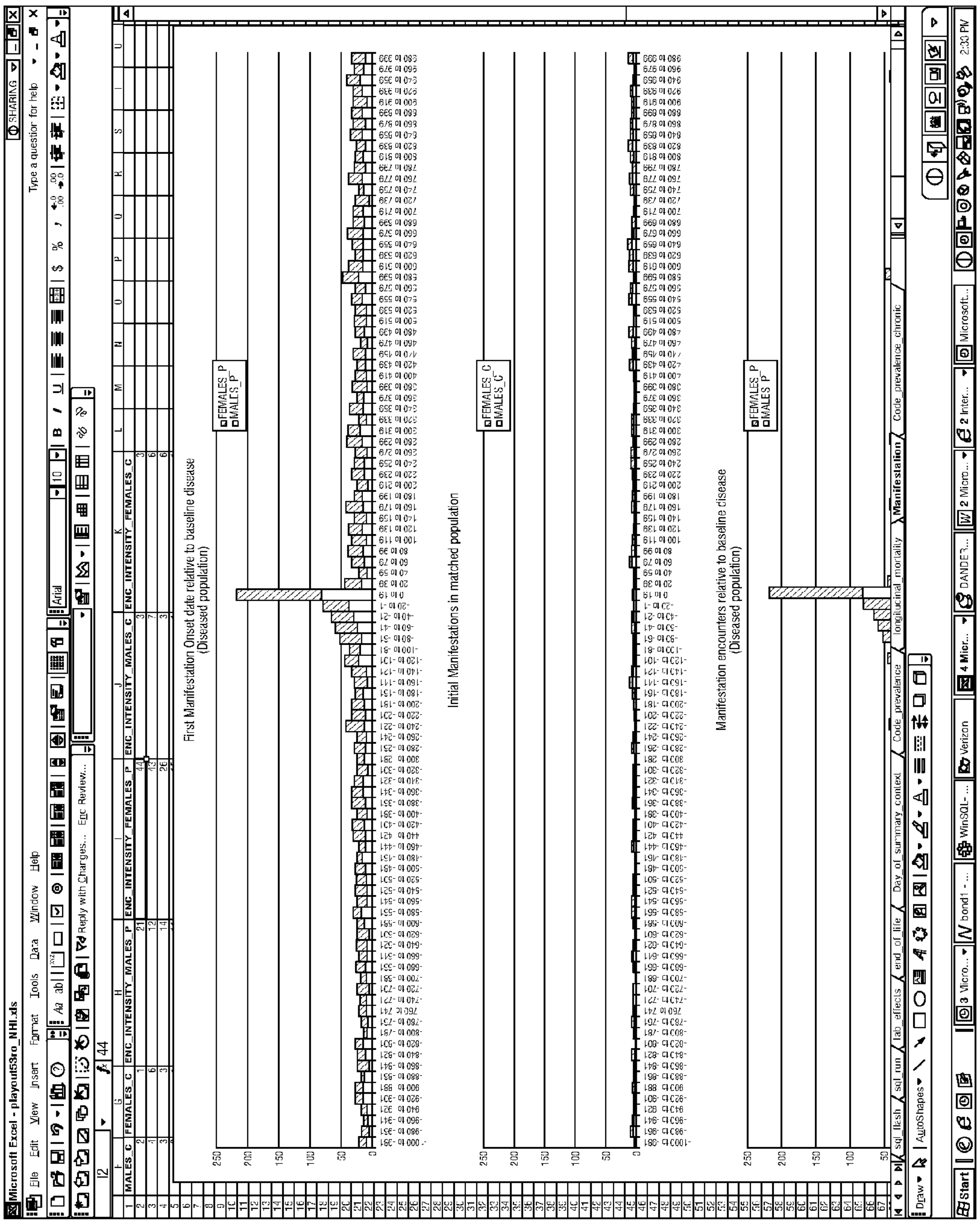
FIG. 13 is a screen-shot diagram illustrating one embodiment of a statistic calculated by rapid cohort analysis.

In certain embodiments, after determination of the index date for each record, the first and second groups of records may be aggregated respectively on the relatively same time frame for comparison as further illustrated in FIG. 13.

The server 102 may also include other modules for computing, formatting, and otherwise producing statistics, including a compute module 712 and a graph module 714. The compute module 712 may compute a probability in response to a ratio of a number of records in the first group having the selected attribute and a number of records in the second group having the selected attribute. The graph may generate, format, and provide a graphical representation of the statistics. These modules 708-714 may be stand-alone modules implemented in hardware, firmware, or software. Alternatively, the functions may be accomplished through commercial calculation products or spreadsheets, or software or SQL instructions that are integrated with the other functions of the server 102. In a specific embodiment, the calculation module 606, including some or all of its component modules 708-714, may communicate the statistics with the interface module 602 for display or communication to a user.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 8:
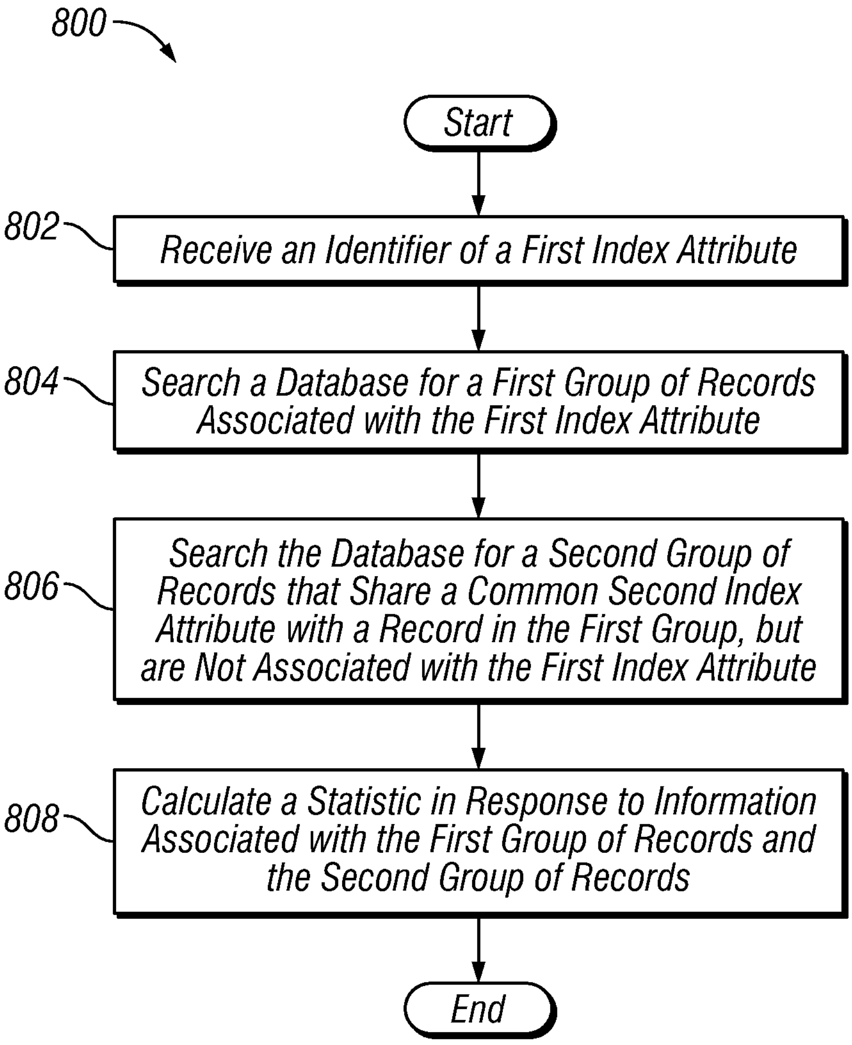
FIG. 8 is a schematic flowchart diagram illustrating one embodiment of a method for rapid cohort analysis.

FIG. 8 illustrates one embodiment of a method 800 for rapid cohort analysis. In one embodiment, the method 800 starts when the interface module 602 receives 802 an identifier of a first index attribute. The method 800 may continue when the processor 302 issues a command to search 804 a database stored on the data storage device 104 for a first group of records. The first group of records may be associated with the first index attribute. For example, the processor 302 may send an SQL query to the database to retrieve healthcare records associated with individuals that have been diagnosed with diabetes as indicated by the presence of an ICD-9 code associated with diagnosis of diabetes in the individual's records.

The processor 302 may then issue a command to search 806 the database for a second group of records. Each record in the second group of records may share a common second index attribute (which could be one or more common attributes) with a record in the first group of records, but not include the first index attribute. For example, SQL query issued by the processor 302 may also include a query statement to search for a second group of individuals, each individual having the same age and/or gender as an individual identified in the first group, but not having the diabetes diagnosis code in their record. These individuals in the second group may be considered cohorts of the individuals in the first group of records.

The server 102 may then receive the results from the database searches 804, 806. The calculation module 608 may then calculate 808 a statistic in response to the information associated with the first group of records and the second group of records. For example, a spreadsheet program may calculate probabilities of being diagnosed with diabetes in the presence of certain identified lab values, other diagnoses, physical conditions, healthcare patterns, weight, age, gender, etc. The statistics may include averages, probabilities, and other computational products including identification of trends and commonalities among the records.

Figure 9:
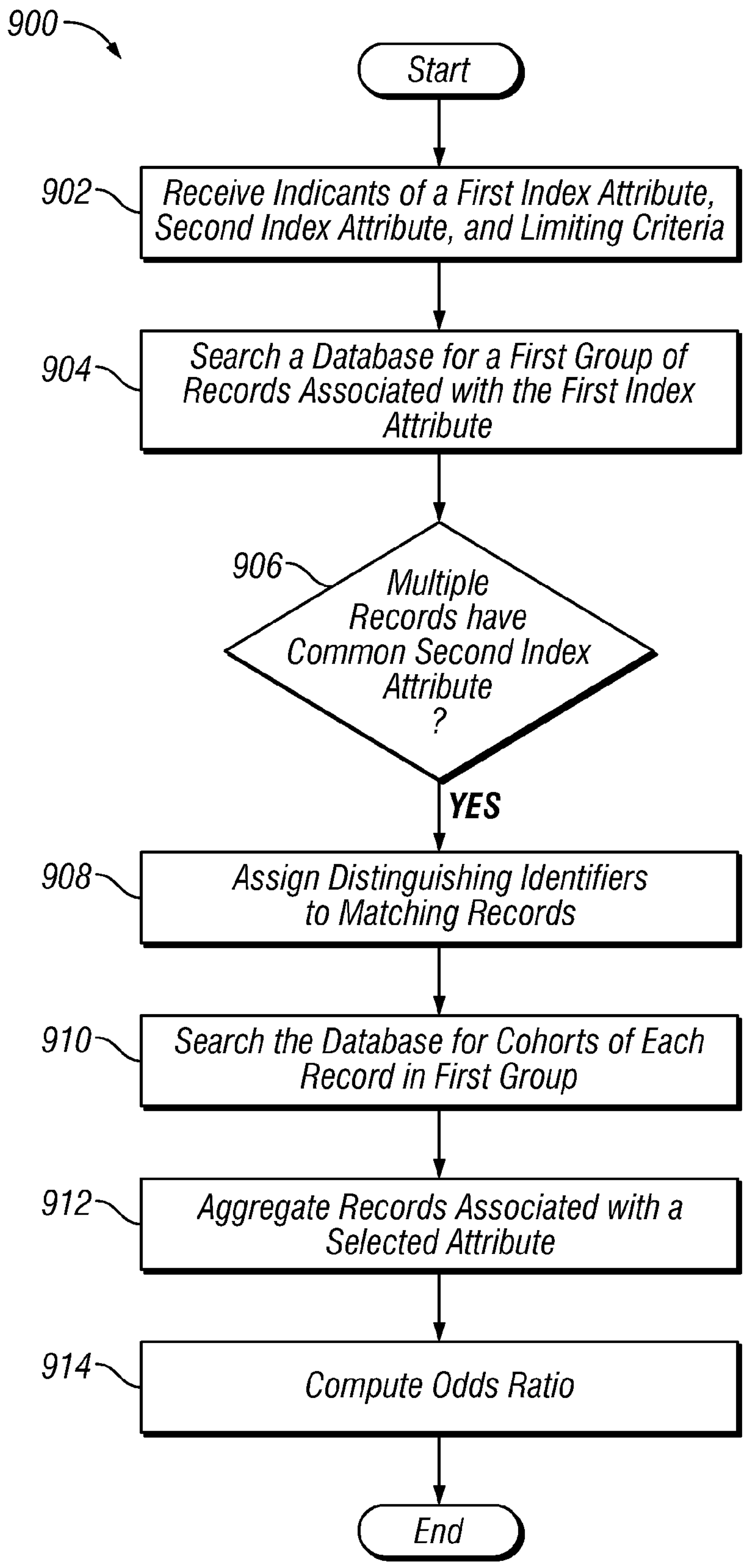
FIG. 9 is a schematic flowchart diagram illustrating another embodiment of a method for rapid cohort analysis.

FIG. 9 illustrates another embodiment of a method 900 for rapid cohort analysis. In one embodiment, the method 900 starts when the interface module 602 receives 902 indicants of a first index attribute, a second index attribute, and one or more limiting criterion. For example, the interface module 602 may include a graphical user interface. The interface module 602 may receive user inputs consisting of identifiers or indicants of the first index attribute and the second index attribute. Such indicants may include a selection of a field value, such as an ICD-9 code value, an age value, a gender value, a minority status, an income level, a geographical value, a therapeutic code, a procedure code, or the like.

Limiting criterion may include windowing values configured to limit or restrict the time frames from which records will be searched, restrictions on minimum enrollment time, minimum number of records, gender restrictions, age restrictions, and other similar threshold and limiting values. The narrowing module 702 may incorporate the limiting criterion into a query used to search 904 the database for the first group of records associated with the first index attribute. For example, the query may search for all records associated with individuals that have been diagnosed with diabetes, but the query may be restricted to return only results associated with individuals that have at least two years worth of records in the database.

If the first assignment module 704 determined 906 that multiple records within the first group of records have common second index attributes, the first assignment module 704 may assign 908 a distinguishing identifier to each matching record. The second search module 606 may then search 910 the database for cohorts of each record in the first group. If it had been determined 906 that multiple records in the first group of records had common second index attributes, the second assignment module 706 may assign a distinguishing identifier to each of the cohort records in the second group of records that correspond to a distinguished record in the first group of records. In such an embodiment, the second search module 606 may identify a cohort for each record in the first group of records.

In one embodiment, the aggregation module 710 may aggregate 912 records from the first group and from the second group according to a selected attribute. An example of aggregation 912 is illustrated in FIG. 10. The compute module 712 may then compute 914 an odds ratio. In an alternative embodiment, the compute module 712 may compute an average, or some other mathematical statistic. In certain further embodiments, the count module 708 may produce a count of records having a selected characteristic, as shown in FIG. 10. In still a further embodiment, the graph module 714 may generate one or more graphs to graphically display one or more statistics calculated by the server 102.

In a specific example, the server may send a single set of SQL instruction to perform the first search 904, assign 908 distinguishing identifiers, perform the second search 910, and other searching functions. In a further embodiment, the SQL instructions may further include instructions for aggregating 912 the records. In still another embodiment, the same set of SQL instructions may include functions for computing 914 statistics, such as the odds ratio of a specified event or occurrence within the records. For example, one embodiment of SQL instructions that may be used to perform the method of FIG. 9 may include:

```
select
iv3.decm_code,iv3.code_desc,primary_count,cohort_count,max
(all_in_primary_count) over (partition by 1)
all_in_primary_count,max(all_in_cohort_count) over (partition by
1) all_in_cohort_count from ( select iv2.decm_code,iv2.code_desc
,sum(case when twin_set='Primary' then count_distinct else 0 end )
primary_count ,sum(case when twin_set='Cohort' then count_distinct
else 0 end ) cohort_count ,max(case when twin_set='Primary' then
tot1 else 0 end ) all_in_primary_count ,max(case when
twin_set='Cohort' then tot1 else 0 end ) all_in_cohort_count from
 ( select a1.decm_code,a1.code_desc,tot1, 'Primary' twin_set ,count
 (distinct   id_primary ) count_distinct
   from
 (
select iv_primary.individual_id id_primary,iv_cohort.individual_id
id_cohort,min_dos, count(1) over (partition by 1) tot1 from (
select *,row_number( ) over (partition by
age_at_onset,year_of_onset,gender order by year_of_onset)
rn_inplay from
 (
select
iv.individual_id,c.gender,min_dos,trunc((min_dos-
date_of_birth)/365.24)
age_at_onset,to_char(min_dos,'yyyy')+0 year_of_onset from ( SELECT
b.individual_id,
         MIN(service_from_date) min_dos
  FROM diagnosis_with_death a,          foo_members_with_condition6
b
WHERE decm_code like 'dxnatasha'
         AND b.dx=a.diagnosis_key
GROUP BY b.individual_id ) iv
,
           foo_2yr_ce_medcohorts c
WHERE iv.individual_id=c.individual_id
             AND min_dos BETWEEN med_start    AND med_end    AND
med_end >=
min_dos+aggend
         AND min_dos-med_start>=clean_period
         )    iv
         )    iv_primary
         ,
 (
select *,row_number( ) over (partition by
age_at_onset2,year_of_onset2,gender order by year_of_onset2)
rn_inplay2 from (
   select trunc((med_start+clean_period+365-date_of_birth)/365.24)
age_at_onset2
   ,to_char(med_start+clean_period+365,'yyyy')+0 year_of_onset2
   ,*    from    foo_2yr_ce_medcohorts c2
         where med_end-med_start>=clean_period+case when aggend>0
then aggend else 0 end+730    and individual_id not in (select
distinct individual_id    FROM diagnosis_with_death
a,foo_members_with_condition6 b
         WHERE decm_code like 'dxnatasha'          AND
b.dx=a.diagnosis_key)
         ) iv
) iv_cohort
where age_at_onset=age_at_onset2 and year_of_onset=year_of_onset2
and iv_primary.gender=iv_cohort.gender and rn_inplay=rn_inplay2
) iv,diagnosis_with_death a1,              foo_members_with_condition6
b1
where (b1.individual_id=id_primary ) and b1.dx=a1.diagnosis_key
```

-continued

```
and service_from_date-min_dos between aggstart and aggend group by
a1.decm_code,a1.code_desc,tot1,twin_set
union
select a1.decm_code,a1.code_desc,tot1, 'Cohort' twin_set ,count
 (distinct id_cohort ) count_distinct
   from
 (
select iv_primary.individual_id id_primary,iv_cohort.individual_id
id_cohort,min_dos, count(1) over (partition by 1) tot1 from (
select *,row_number( ) over (partition by
age_at_onset,year_of_onset,gender order by year_of_onset)
rn_inplay from
 (
select
iv.individual_id,c.gender,min_dos, trunc((min_dos-
date_of_birth)/365.24)
age_at_onset,to_char(min_dos,'yyyy')+0 year_of_onset from ( SELECT
b.individual_id,
           MIN(service_from_date) min_dos
  FROM diagnosis_with_death a,              foo_members_with_condition6
b
WHERE decm_code like 'dxnatasha'
           AND b.dx=a.diagnosis_key
GROUP BY b.individual_id ) iv
,
            foo_2yr_ce_medcohorts c
WHERE iv.individual_id=c.individual_id
                AND min_dos BETWEEN med_start      AND med_end AND
med_end >=
min_dos+aggend
           AND min_dos-med_start>=clean_period
           )    iv
           )    iv_primary
           ,
(
select *,row_number( ) over (partition by
age_at_onset2,year_of_onset2,gender order by year_of_onset2)
rn_inplay2 from (
   select trunc((med_start+clean_period+365-date_of_birth)/365.24)
age_at_onset2
   ,to_char(med_start+clean_period+365,'yyyy')+0 year_of_onset2
   ,*    from        foo_2yr_ce_medcohorts c2
           where med_end-med_start>=clean_period+case when aggend>0
then aggend else 0 end+730 and individual_id not in (select
distinct individual_id FROM diagnosis_with_death
a,foo_members_with_condition6 b
           WHERE decm_code like'dxnatasha'           AND
b.dx=a.diagnosis_key)
           ) iv
) iv_cohort
where age_at_onset=age_at_onset2 and year_of_onset=year_of_onset2
and iv_primary.gender=iv_cohort.gender and rn_inplay=rn_inplay2
) iv,diagnosis_with_death a1,              foo_members_with_condition6
b1
where (b1.individual_id=id_cohort ) and b1.dx=a1.diagnosis_key and
service_from_date-min_dos between aggstart and aggend group by
a1.decm_code,a1.code_desc,tot1,twin_set
) iv1, ( select decm_code,code_desc,row_number( ) over (partition
by decm_code order by update_date desc) rn FROM
diagnosis_with_death where code_desc not like 'UNKNOWN
DIAGNOSIS')
iv2 where iv1.decm_code=iv2.decm_code and rn=1 group by
iv2.decm_code,iv2.code_desc ) iv3
```

FIG. 10 illustrates one embodiment of an output table 1000 that may be compiled from the first group of records and the second group of records. In this embodiment, the table includes a field for a diagnosis code. The diagnosis code may be the selected attribute. The table 1000 may also include one or more fields for displaying count results. The count fields may include a count of individuals in the first or primary group having the specified diagnosis code present in their records and a count of the number of cohorts also having the diagnosis code present in their records. The table 1000 may also include one or more fields for calculating statistics. For example, in the table 1000 the p_OR field and the q_OR field include values for a numerator and a denominator of an odds ratio statistic for each of the diagnosis codes.

The embodiment of the table 1000 described in FIG. 10 illustrates one method for calculating and displaying statistics. In this embodiment, a first group of records may be collected for individuals having been diagnosed with diabetes. In such an embodiment, the diagnosis code for diabetes may be the first index attribute. The second group of individuals (cohorts of the individuals in the first group) may be collected. The cohorts may have the same age, gender, or some other second index attribute. The number of individuals or records identified in the searches may be limited by limiting criterion. The results may then be aggregated and statistics may be calculated for one or more selected attributes. For example, in the table 1000 of FIG. 10, the selected attributes are diagnosis codes for potential co-morbid conditions.

Figure 11:
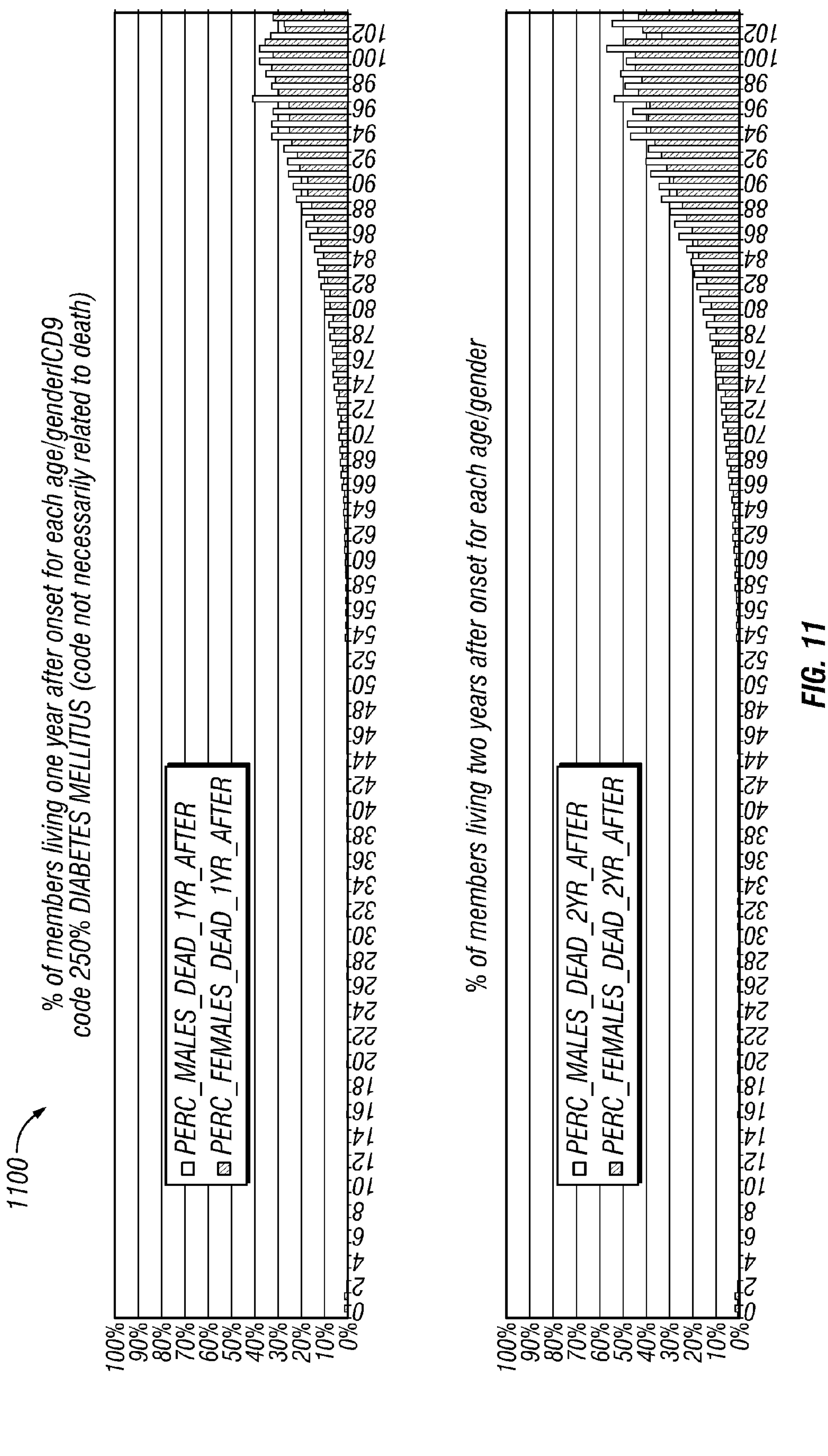
FIG. 11 is a chart illustrating another embodiment of a statistic calculated by rapid cohort analysis.

FIG. 11 illustrates one embodiment of a graphical statistic output 1100. In one embodiment, the statistics may be formatted into a graphical presentation. For example, the graph 1100 includes a graphical illustrating the impact on survivability of those diagnosed with diabetes as compared to those of the general population (% dead within one year of onset, % dead within two years of onset). These charts may be generated through the rapid cohort analysis described herein, if the index attribute is chosen as diabetes and the "Death" attribute is aggregated matching the charts one or two year post onset periods. In this embodiment, the graph 1100 is a bar graph format. Alternative embodiments may include pie charts, venn diagrams, histograms, line diagrams, and the like.

Figure 12:
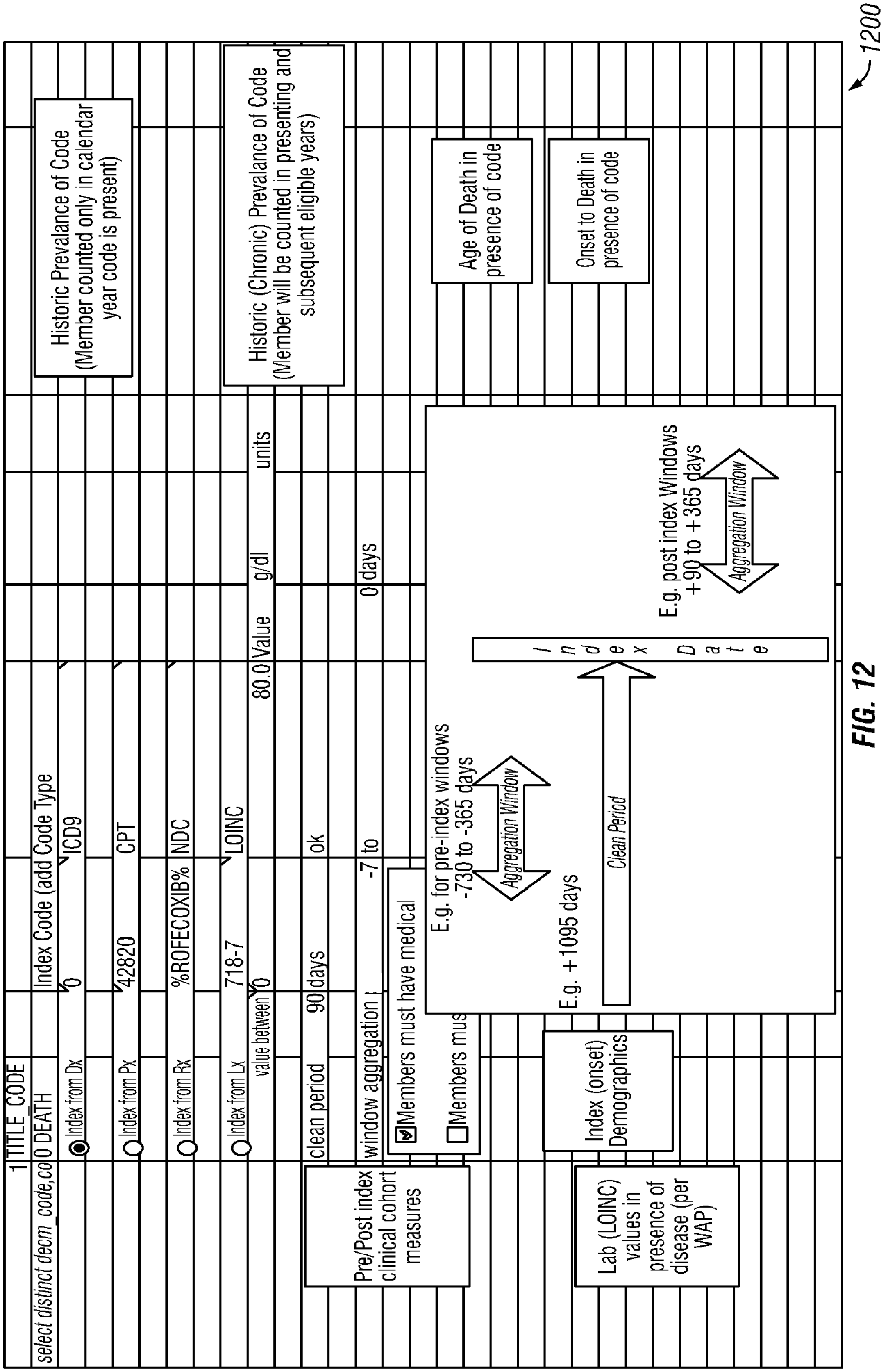
FIG. 12 is a screen-shot diagram illustrating one embodiment of a graphical user interface for rapid cohort analysis.

FIG. 12 illustrates one embodiment of a graphical user interface (GUI) 1200 for use in accordance with the interface module 602. As illustrated, the GUI 1200 may include one or more fields for receiving user inputs, one or more buttons for issuing a command or controlling the server, application, or code, and one or more descriptive or informational names or elements for providing user instructions and prompts. As illustrated in the informational diagram in FIG. 12, certain limiting criteria may include a clean period value, or time period prior to the occurrence of the first index attribute. For example, if the first index attribute is a diagnosis code for diabetes, the clean period criteria may be a time frame, such as two years, before the occurrence of the diagnosis code. In such an embodiment, the first search module 604 may only return records for individuals who have not only been diagnosed with diabetes, but also have a minimum of two years worth of records prior to the diagnosis.

FIG. 13 illustrates one embodiment of a graphical statistic output 1300. In one embodiment, the statistics may be formatted into a graphical presentation. For example, the graph 1300 includes a graphical illustrating the temporal distribution of the diseased population (for example, the index date or time 0 would be onset date of the disease, such as diabetes) and the matched population (e.g., non-diabetic but could be obese or not; the index date would be set arbitrarily or specifically as described above). These graphs may be generated through the rapid cohort analysis described herein, if the first index attribute is chosen as a disease. The records of the first (diseased) and second group (matched, e.g., non-diseased or a general population) could be aggregated by calculating total numbers of records (as illustrated by the y-axis) based on a determined index date as onset and a time scale of a plurality of temporal ranges pre-onset or post-onset (as illustrated by the x-axis). In this embodiment, the graph 1300 is a bar graph format. Alternative embodiments may include pie charts, venn diagrams, histograms, line diagrams, and the like.

The limiting criteria may also include an aggregation window, or time frame for collecting records associated with the individual. The aggregation window variable may include a time frame before or after the occurrence of the first index attribute from which to collect records. For example, the narrow module 702 may only collect records for two years prior to the occurrence of the diagnosis code and for ninety days after the occurrence of the diagnosis code.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. An apparatus, comprising:

an interface configured to receive an identifier of a first index attribute and a second index attribute; and a processor in data communication with the interface, the processor configured to:

search the database for a first group of healthcare records associated with the first index attribute;

assign a first distinguishing identifier to each healthcare record in a subset of the first group of healthcare records in response to a determination that the subset of healthcare records have a common value of a second index attribute;

search the database for a second group of cohort healthcare records, wherein each cohort healthcare record in the second group of cohort healthcare records shares a common second index attribute with a healthcare record in the first group of healthcare records, but not associated with the first index attribute;

assign a second distinguishing identifier to each cohort record in the second group of cohort healthcare records that corresponds to the first distinguishing identifier assigned to a healthcare record in the subset of the first group of healthcare records; and calculate a statistic in response to healthcare information associated with the first group of healthcare records and the second group of cohort healthcare records based on the assigned first and second identifiers, wherein the statistic comprises a probability of an attribute shared between a diagnosis for a person represented by a healthcare record in the second group and a diagnosis for a person represented by a healthcare record in the first group.

2. A system, comprising:

a data storage device configured to store a healthcare database comprising one or more healthcare records, each healthcare record having one or more attributes; and a server in data communication with the data storage device, configured to:

receive an identifier of a first index attribute and a second index attribute;

search the database for a first group of healthcare records associated with the first index attribute;

assign a first distinguishing identifier to each healthcare record in a subset of the first group of healthcare records in response to a determination that the subset of healthcare records have a common value of a second index attribute;

search the database for a second group of cohort healthcare records, wherein each cohort healthcare record in the second group of cohort healthcare records shares a common second index attribute with a healthcare record in the first group of healthcare records, but not associated with the first index attribute; and calculate a statistic in response to healthcare information associated with the first group of healthcare records and the second group of cohort healthcare records based on the assigned first and second identifiers, wherein the statistic comprises a probability of an attribute shared between a diagnosis for a person represented by a healthcare record in the second group and a diagnosis for a person represented by a healthcare record in the first group.

3. The system of claim 2, where the server is further configured to narrow the first group of healthcare records according to a limiting criterion.

4. The system of claim 2, where the server is further configured to count distinct healthcare records in the first group of healthcare records and the second group of healthcare records.

5. The system of claim 2, where the server is further configured to aggregate healthcare records from the first group and from the second group according to a selected attribute.

6. The system of claim 5, where the server is further configured to compute a probability in response to a ratio of a number of healthcare records in the first group having the selected attribute and a number of healthcare records in the second group having the selected attribute.

7. A computer program product, comprising a non-transitory computer readable medium having computer usable program code executable to perform operations comprising:

receiving an identifier of a first index attribute and a second index attribute;

searching a database for a first group of healthcare records associated with the first index attribute;

assigning a first distinguishing identifier to each healthcare record in a subset of the first group of healthcare records in response to a determination that the subset of healthcare records have a common value of a second index attribute;

searching the database for a second group of cohort healthcare records, wherein each cohort healthcare record in the second group of cohort healthcare records shares a common second index attribute with a healthcare record in the first group of healthcare records, but not associated with the first index attribute;

assigning a second distinguishing identifier to each cohort record in the second group of cohort healthcare records that corresponds to the first distinguishing identifier assigned to a healthcare record in the subset of the first group of healthcare records; and calculating a statistic in response to healthcare information associated with the first group of healthcare records and the second group of healthcare records based on the assigned first and second identifiers, wherein the step of calculating the statistic comprises calculating a probability of an attribute shared between a diagnosis for a person represented by a healthcare record in the second group and a diagnosis for a person represented by a healthcare record in the first group.

8. The computer program product of claim 7, wherein the code also performs the operation of narrowing the first group of healthcare records according to a limiting criterion.

9. The computer program product of claim 7, wherein calculating the statistic further comprises counting distinct healthcare records in the first group of healthcare records and the second group of healthcare records.

10. The computer program product of claim 7, wherein calculating the statistic further comprises aggregating healthcare records from the first group and from the second group according to a selected attribute.

11. The computer program product of claim 10, wherein calculating the statistic further comprises computing a probability in response to a ratio of a number of healthcare records in the first group having the selected attribute and a number of healthcare records in the second group having the selected attribute.

12. A method, comprising:

receiving an identifier of a first index attribute and a second index attribute;

searching a database for a first group of healthcare records associated with the first index attribute;

assigning a first distinguishing identifier to each healthcare record in a subset of the first group of healthcare records in response to a determination that the subset of healthcare records have a common value of a second index attribute;

searching the database for a second group of cohort healthcare records, wherein each cohort healthcare record in the second group of cohort healthcare records shares a common second index attribute with a healthcare record in the first group of healthcare records, but not associated with the first index attribute;

assigning a second distinguishing identifier to each cohort record in the second group of cohort healthcare records that corresponds to the first distinguishing identifier assigned to a healthcare record in the subset of the first group of healthcare records; and calculating a statistic in response to healthcare information associated with the first group of healthcare records and the second group of cohort healthcare records based on the assigned first and second identifiers, wherein calculating a statistic comprises a probability of an attribute shared between a diagnosis for a person represented by a healthcare record in the second group and a diagnosis for a person represented by a healthcare record in the first group.

13. The method of claim 12, further comprising narrowing the first group of healthcare records according to a limiting criterion.

14. The method of claim 12, wherein calculating the statistic further comprises counting distinct healthcare records in the first group of healthcare records and the second group of healthcare records.

15. The method of claim 12, wherein calculating the statistic further comprises aggregating healthcare records from the first group and from the second group according to a selected attribute.

16. The method of claim 15, wherein calculating the statistic further comprises computing a probability in response to a ratio of a number of healthcare records in the first group having the selected attribute and a number of healthcare records in the second group having the selected attribute.

* * * * *